United States Patent [19]

Fanning

[11] Patent Number: 5,280,108
[45] Date of Patent: Jan. 18, 1994

[54] ANTIBODIES TO P40

[75] Inventor: Thomas G. Fanning, Gaithersburg, Md.

[73] Assignee: United States of America, Washington, D.C.

[21] Appl. No.: 750,044

[22] Filed: Sep. 27, 1991

[51] Int. Cl.$^5$ .................. A61K 35/16; C07K 15/28
[52] U.S. Cl. .................. 530/387.7; 530/388.3; 530/388.8; 530/389.4; 530/389.7; 530/391.3; 530/391.5; 435/70.21; 435/172.2; 435/240.27; 436/501; 436/536
[58] Field of Search ............. 530/387.7, 388.3, 388.8, 530/389.4, 389.7, 391.3, 391.5; 435/70.21, 172.2, 240.27; 436/501, 536

[56] References Cited

PUBLICATIONS

Bratthauer, et al Oncogene 7:507 1992.
Renauld, et al JI 144:4235-4241 1990.
Oellerich J. Clin Chem Clin Biochem 22(12)895 1984.
Hanlow et al Antibodies a Laboratory Manual 1988 Cold Spring Hanbor Press.
Skowronski, J. et al., "Unit-Length Line-1 Transcripts in Human Teratocarcinoma Cells," Molecular and Cellular Biology, Apr. 1988, pp. 1385-1397.
Leibold, Debra M. et al., "Translation of Line-1 DNA elements in vitro and in human cells," Proc. Natl. Acad. Sci. U.S.A., vol. 87, pp. 6990-6994, Sep. 1990.

Primary Examiner—David L. Lacey
Assistant Examiner—Donab E. Adams
Attorney, Agent, or Firm—Knobbe, Martens, Olson & Bear

[57] ABSTRACT

The present invention relates, in general, to antibodies to p40 (both polyclonal and monoclonal). Additionally, the present invention relates to hybridomas which produce monoclonal antibodies to p40 and diagnostic kits comprising antibodies to p40.

9 Claims, 3 Drawing Sheets

ANTIBODIES TO P40

BACKGROUND OF THE INVENTION

1. Field of the Invention

The present invention relates, in general, to antibodies. In particular, the present invention relates to antibodies to p40.

2. Background Information

LINE-1 is a mammalian retrotransposon (Fanning, T. G. & Singer, M. F. (1987) Biochim. Biophys. Acta 910:203-212; Hutchison, C. A. et al. (1989) Mobile DNA, Berg, D. E. & Howe, M. M. (eds.) Am. Soc. Microbiol., Washington DC. pp. 593-617; Singer, M. F. et al. (1988) Banbury Report 30: Eukaryotic Transposable Elements as Mutagenic Agents. Cold Spring Harbor Press, New York. pp. 71-78). The human element has an internal RNA polymerase promoter (Swergold G. D. (1990) Mol. Cell. Biol. 10:6718-6729) and two open reading frames, the first of which encodes a protein (p40) of ca. 40 kd with no known function (Skowronski, J. et al. (1988) Mol. Cell. Biol. 8:1385-1397). Human LINE-1 sequences (L1Hs) make up about 5% of the human genome and most are defective, primarily due to truncation and internal rearrangements (Grimaldi, G. et al. (1984) EMBO J. 3:1753-1759). Most full length, unrearranged elements are also defective since they contain open reading frames interrupted by stop codons (Skowronski, J. et al. (1988) Mol. Cell. Biol. 8:1385-1397). Nevertheless, functional (transposable) elements must exist since de novo integrations have been observed in three individuals: in two cases there were integrations into factor VIII genes (Kazazian, H. H. et al. (1988) Nature 332:164-166) and in one case into a c-myc allele (Morse, B. et al. (1988) Nature 333:87-90).

Previous studies have suggested that L1Hs are not active in most cells since specific transcripts were not detected by Northern blotting and/or primer extension (Skowronski, J. & Singer, M. F. (1985) Proc. Natl. Acad. Sci. U.S.A. 82:6050-6054; Skowronski, J. & Singer, M. F. (1986) Cold Spring Harbor Symp. Quant. Biol. 51:457-464). Exceptions were cell lines derived from cancers of epithelial origin; in several cell lines derived from human testicular germ cell tumors (teratocarcinomas) L1Hs-specific RNA and proteins were detected and transcription appeared to be regulated since it was observed only in undifferentiated cells (Skowronski, J. & Singer, M. F. (1985) Proc. Natl. Acad. Sci. U.S.A. 82:6050-6054; Skowronski, J. & Singer, M.F. (1986) Cold Spring Harbor Symp. Quant. Biol. 51:457-464; Skowronski, J. et al. (1988) Mol. Cell. Biol. 8:1385-1397). The exact meaning of these observations is not clear, however, since cell lines may represent minor species present within the tumor mass (Brawn, P. N. (1987) Cancer 59:2042-2046; Loehrer, P. L. et al. (1987) Semin. Oncol. 12:304-316). In addition, cell lines have often been so "massaged" by the experimenter that it may be idealistic to expect that they faithfully reflect the characteristics of their progenitors in the tumor of origin (Andrews, P. W. et al. (1987) Teratocarcinomas and Embryonic Stem Cells. Robertson, E. J. (ed.). IRL Press, Oxford. pp. 207-248). Therefore, the present invention provides antibodies to p40 for examining tumors for L1Hs expression.

SUMMARY OF THE INVENTION

It is a object of this invention to provide an antibody having binding affinity to p40, or a unique portion thereof.

It is another object of the invention to provide a hybridoma which produces a monoclonal having binding affinity to p40, or a unique portion thereof.

It is a further object of the invention to provide a diagnostic kit comprising an antibody having binding affinity to p40, or a unique portion thereof.

Further objects and advantages of the present invention will be clear from the description that follows.

BRIEF DESCRIPTION OF THE DRAWINGS

(FIG. 1A) Schematic drawing of L1Hs unit element based on consensus sequence. Hatching indicates noncoding and inter-ORF regions. Typical restriction endonuclease sites are shown: A, Acc I; B, BamHI; Bg, Bgl 11; E, EcoRI; K, Kpn1; S, Sac I. (FIGS. 1B-1J) Black areas represent the L1Hs region present in the plasmids p11A, p12A, p14A, p16A, and p1 (FIG. 1B); p11ASac (FIG. 1C); p11AKpn (FIG. 1D); p23A (FIG. 1E); pL1.1 (FIG. 1F); p3HS1 (FIG. 1G); p3HS3 (same insert but reverse orientation compared to p3HS1) (FIG. 1H); p1LZ (FIG. 1I); and p3LZ (FIG. 1J). The vectors in which the various inserts are contained are described in Materials and Methods.

(FIG. 3A) Lane 1, 20 μg of protein from E. coli transfected with p3HS1; lane 2, 20 μg of protein from E. coli transfected with p3HS3. (FIG. 3B) Lanes 1 and 2, 43 μg of protein from NTera2D1; lane 3, 25 μg of protein from 2102Ep; lane 4, 35 μg of protein from JFG-3; lane 5, 45 μg of protein from 293; 160 μg of protein from HeLA; lane 7, 20 μg of protein from HL-60.

(FIG. 4A), lanes 3 and 4); and p3LZ (FIG. 4A) lanes 5 and 6; (FIG. 4B) lanes 1 and 2).

(FIG. 6A) tumor from patient #1 plus AH40.1; FIG. 6B tumor from patient #1 plus preimmune serum FIG. 6C tumor from patient #2 plus AH40.1; FIG. 6D from patient #2 plus preimmune serum.

DETAILED DESCRIPTION OF THE INVENTION

Figure 1:
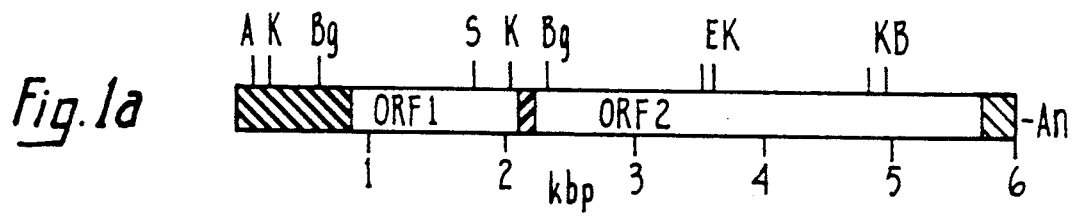
FIGS. 1A-1J. Diagram of L1Hs element (FIG. 1A) and construction (FIGS. 1B-1J) utilized in the present experiments.

Germ cell cancers often metastasize and these metastatic cells can sometimes be identified by antibodies to certain cellular proteins. However, these proteins are often produced in normal cells also. Antibodies against the LINE-1 p40 protein are herein shown to detect the presence of p40 protein in tissue sections and cells by immunohistochemistry and in cell extracts by Western blotting. The p40 protein is shown to be made in detectable amounts in malignant epithelial cells and detectable expression of LINE-1 appears to be restricted to malignant cells.

In one embodiment, the present invention relates to p40 antibodies (polyclonal or monoclonal), or binding fragments thereof. Polyclonal antibody AH40.1 is preferred.

The monoclonal antibodies of the invention can be produced by hybridomas, advantageously murine hybridomas. For example, mice can be immunized with the p40 protein, a booster inoculation can be given, and, after a time sufficient to induce an immune response, the mouse is sacrificed and the spleen and/or lymph cells are obtained and fused, advantageously, with myeloma cells, using known techniques. The resulting cells, which include the fused hybridomas, are allowed to grow in a selective medium, such as HAT-medium, and the surviving cells are grown in such medium using limiting dilution conditions. The cells are grown in a suitable container, e.g., microtitre wells, and the supernatants are screened for monoclonal antibodies having the desired specificity.

The invention also relates to useful binding fragments of the p40 specific monoclonal antibodies. The antibody fragments are obtained by conventional techniques. For example, useful binding fragments can be prepared by digestion of the antibody using papain or pepsin.

While the above-specified examples of the antibodies of the invention are of the IgG class and are from a murine source, this is not meant to be a limitation. The specified antibodies and antibodies functionally equivalent thereto (that is, capable of binding to the above-described p40 protein antigens whether from a murine source, mammalian source, including human, or other sources, or combinations thereof, are included within the scope of this invention, as are antibodies of other classes such as IgA, IgM, IgE, and the like, including isotypes within such classes.

Various conventional methods exist for isolation and purification of the monoclonal antibodies, so as to free monoclonal antibodies from other proteins and other contaminants (see, for example, Goding, in *Monoclonal Antibodies: Principals and Practice*, Chapter 4, 1986; the entire contents of which document is hereby incorporated by reference).

The invention also relates to a diagnostic kit for use in detecting the presence of p40 containing cells in a biological sample, which kit is based, for example, on the method described above. In one embodiment, the diagnostic kit comprises (i) the polyclonal or monoclonal antibody or antibodies (or binding fragment(s) thereof) as defined above, and (ii) a conjugate of a specific binding partner for the monoclonal antibody and a label capable of producing a detectable signal. Reagents, such as ancillary agents, for example, buffering agents and protein stabilizing agents and the like, can also be included. The diagnostic kit can further include, where necessary, other members of the signal producing system, of which system the label is a member, agents for reducing background interference in a test, control reagents, and apparatus for conducting a test. In another embodiment, the diagnostic kit comprises a conjugate of a monoclonal antibody or antibodies of the invention and a label capable of producing a detectable signal. Ancillary agents as mentioned above can also be present.

The present invention is described in further detail in the following non-limiting examples.

EXAMPLES

The following protocols and experimental details are referenced in the Examples that follow:

Construction of Plasmids.

Subcloned EcoRI segments representing the 5' portions of the previously cloned L1Hs cDNAs (the cD-A plasmid clones described in Skowronski, J. et al. (1988) Mol. Cell. Biol. 8:1385–1397) were inserted into the multiple cloning site of Bluescript pKS(+) vector (Strategene) to generate p11A, p12A, p14A, and p16A ($\approx$3.4-kbp L1Hs insert; FIG. 1*b*) and p23A ($\approx$1.5-kbp insert; FIG. 1*e*). Orientation of the L1Hs segment with respect to the promoters for T7 and T3 phage RNA polymerases in the vector was determined by restriction endonucleases mapping. Deleted derivatives p11ASac and p11AKpn (FIG. 1 *c* and *d*) were prepared by cleavage of p11A with Sac I or Kpn I and religation. A segment of the full-length L1Hs element in phage λMA1, representing residues 40–3549, was inserted into the Acc I and EcoRI sites of pKS(+) to produce pλ1 (FIG. 1*b*); λMA1 was isolated from a human genomic library in λ Charon 4A (Maniatis, T. et al., (1978) Cell 15, 687–701). Another recombinant plasmid, pL1.1, containing the first 41 L1Hs residues from p1LZ (FIG. 1*i*) followed by residue 42 to the 3' end of the full-length genomic L1Hs (L1.1) inserted into the multiple cloning site of pGEM-5Zf (Promega) (FIG. 1*f*), was also used. The L1Hs elements in both λMA1 and L1.1 belong to a subset of L1hs elements, called Ta, that is well represented in NTera2D1 L1 RNA (Skowronski, J. et al., (1988) Mol. Cell. Biol. 8, 1385–1397).

An ORF1-containing restriction fragment of cD11 (residues 936-2296) was obtained by using deletions constructed with ExoIII and ExoVII. The 5'-proximal 3.4 kbp of cD11 (cD11A) was cloned into the phage vector M13mp18, and approximately 5 μg of replicative-form DNA was digested to completion with restriction enzymes BamHI (insert proximal) and SphI (insert distal). The DNA was then treated with ExoIII and ExoVII as described previously (Yanisch-Perron, C. et al. (1985) Gene 33:103-119). The DNA was treated with Klenow polymerase I and T4 DNA ligase, and samples of the ligated materials were transfected into Escherichia coli JM101. Clear plaques were selected and the size of the M13 recombinant DNAs was determined. The phage DNAs containing deletions of the appropriate sizes were used for DNA sequence determination by the dideoxy method (Sanger, F. et al. (1977) Proc. Natl. Acad. Sci. USA 74:5463-5467).

One of the deleted inserts was inserted into the pATH3 vector (kindly supplied by S. Goff; Tanese et al. (1985) Proc. Natl. Acad. Sci. USA 82:4944-4948) to generate p3HS1 (FIG. 1g), in which L1Hs ORF1 follows the Escherichia coli trpE gene in frame. Sequence analysis confirmed the expected junctions. The fragment of cD11 present in pHS1 includes 24 codons 5' of the first ATG in the fully open ORF1 as well as 338 codons from the ATG to a TAA stop (Skowronski, J. et al., (1988) Mol. Cell. Biol. 8, 1385-1397). In the control plasmid p3HS3 (FIG. 1h) the same L1Hs fragment was fused to the trpE gene. of pATH3 in the opposite orientation. Sequence analysis of the junctions of p3HS3 demonstrated that a stop codon was generated 31 codons into the inserted fragment.

p1LZ and p3LZ were used to transfect human cells. Both contain L1Hs segments inserted, in frame, 5' of the lacZ coding region in the Bluescript pKS(+) vector. p1LZ (FIG. 1i) contains an ≈900-bp L1Hs 5' leader followed by the first 15 residues of cD11 ORF1 fused to the lacZ gene. p3LZ (FIG. 1j) contains the same L1Hs leader followed by a region of cD11 extending through the open ORF1, the inter-ORF sequence, and the first 16 codons of ORF2 followed by the lacZ gene. In both constructs, lacZ is followed by the L1Hs 3' trailer including the polyadenylylation signal, cloned form the hemophiliac patient JH-27 (Kazazian, H.H., Jr. et al. (1988) Nature (London) 332, 164-166).

In Vitro Transcription.

In vitro transcription was carried out utilizing 1 μg of plasmid DNA that had been linearized with an appropriate restriction endonuclease. Transcription conditions were those recommended by the transcription kit supplier (Promega). Unless otherwise indicated, all the RNAs were capped. To prepare capped RNA, the analogue $m^7G(5'')ppp(5')G$ (Boehringer Mannheim) was added (500 μM) to the reaction mixture and the concentration of GTP was decreased to 20 μM (Darveau, A. et al., (1985) Proc. Natl. Acad. Sci. USA 82, 2315-2319). Fidelity of RNA transcription was monitored by agarose gel electrophoresis and the bulk of the RNA was found to be the size of the expected L1Hs transcripts.

In Vitro Translation

Unless otherwise stated, ≈2 μg of RNA was added to a rabbit reticulocyte lysate translation mix (Promega) containing RNasin and [$^{35}$S]methionine. Translation was carried out for 1 hr. at 30° C.

Isolation of Fusion Protein

Figure 3A:
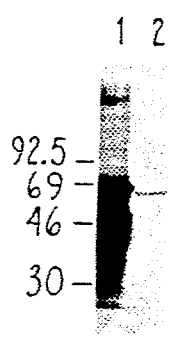
FIGS. 3A-3B. Western blot analysis of extracts from E. coli (FIG. 3A) and several human cell lines (FIG. 3B). A 7% Laemmli gel was utilized. The blots were probed with preadsorbed HS1 antiserum at a 1:1000 fold dilution except in lane 1 of B where matched, preadsorbed preimmune serum was used. Sizes of protein markers are indicated.

E. coli cells containing the p3HS1 vector was grown and induced as described (Tanese, N. et al., (1985) Proc. Natl. Acad. Sci. USA 82, 4944-4948). A protein extract was prepared and run on a preparative polyacrylamide gel. The region of the gel corresponding to the fusion protein (65-90 kDa) was excised and the proteins were eluted. The recovered protein was dialyzed against phosphate-buffered saline containing 0.1% SDS. This partially purified 76-kDa trpE-L1Hs ORF1 (36.2 kDa plus 39.8 kDa) fusion protein was used to immunize rabbits. The resulting HS1 antiserum was preadsorbed with acetone-precipitated total cell extract made form, E. coli containing p3HS3 and expressing the p3HS3 proteins. Such preadsorption eliminated most of those antibodies which were raised to TrpE epitopes or to other bacterial proteins that contaminated the antigen preparation (FIG. 3A, lane 2).

The preadsorbed antiserum was characterized in several ways. Western blot analysis demonstrated that it recognized the trpE-L1Hs ORF1 fusion protein as well as multiple degradation products present in extracts of E. coli that had been transfected with p3HS1 (FIG. 3A, lane 1). No such proteins were recognized by the preadsorbed preimmune serum. That the antibodies were recognizing the L1Hs ORF1-encoded protein was further indicated by the fact that the preadsorbed antiserum could immunoprecipitate the ORF1-encoded polypeptide produced during the in vitro translation of RNA transcribed from p11A. This in vitro synthesized polypeptide was not recognized by antibodies generated against a comparable trpE-L1 Md (Mus domesticus) ORF1 fusion protein. In addition, the antibodies generated against the trpE-L1Hs ORF1 fusion protein did not react with the trpE-L1 Md ORF1 fusion protein, indicated that the HS1 antibodies are specific for the L1Hs ORF1-encoded protein. The species specificity of the antibodies s not surprising, because the predicted L1Hs and L1Md ORF1-encoded proteins share only 35% overall homology at the amino acid level (Skowronski, J. et al., (1988) Mol. Cell. Biol. 8, 1385-1397).

Preparation of Cellular Extracts

Extracts were prepared from several human cell lines: teratocarcinoma cell lines NTera2D1 (19) and 2102Ep (Andrews, P.W. et al., (1989=0) Int. J. Cancer 26, 269-280); JEG-3 choriocarcinoma cells, HeLa epidermoid carcinoma cells, and 293 embryonal kidney cells (American Type Culture Collection); and HL-60 promyelocytic leukemia cells (Gallagher, R. et al., (1979) Blood 54, 713-733). After harvesting by centrifugation, cells were resuspended in lysis buffer (40 mM Tris, pH 7.8/5 mM EDTA/150 mM NaCl) and disrupted by successive freezing and thawing. After centrifugation at 10,000 × g for 5 min. at 4° C., the supernatant was collected and analyzed.

Polyacrylamide Gel Electrophoresis and Autoradiography

Samples were analyzed by polyacrylamide gel electrophoresis under denaturing conditions (Laemmli, U. K., (1970) Nature (London) 227, 680-685). In the case of in vitro translation, polypeptide products were detected by autoradiography of the dried gels.

Western Blot Analysis

Following electrophoresis, extracts were electroblotted onto Immobilon-P membrane (Millipore). Blots were blocked with 5% nonfat dry milk (Food Club) in phosphate-buffered saline at 4° C. overnight (Johnson, D. A. et al., (1984) Gene. Anal. Tech. 1, 3–8). Blots were probed with a 1:1000 dilution of serum (HS1 antiserum or matched preimmune serum) that had been readsorbed with acetone-precipitated total cell extract made from *E. coli* containing p3HS3. The antigen-antibody complex was visualized using biotinylated secondary antibody and avidin-biotinylated horseradish peroxidase complex (Vectastain ABC Kit, Vector Laboratories) in conjunction with the color-developing reagent 4-chloronaphthol (BioRad).

Analysis with AH40.1

All tissues were obtained from the tissue repository at the Armed Forces Institute of Pathology and were formalin-fixed and embedded in paraffin. Immunostaining was done with antibody dilutions of 1:200 and a swine-antirabbit/rabbit-antiperoxidase/peroxidase detection system.

The antibody used in this work is designated AH40.1 and is directed against the 40 kd protein (p40) encoded by the first open reading frame of the L1Hs element. AH40.1 was prepared by injecting rabbits with a TrpE-p40 fusion protein. As a control, AH40.1 was absorbed with acetone powders derived from an *E. coli* strain harboring the fusion protein, and also from a genetically identical strain not containing the fusion protein. Preincubation with the fusion protein abolished AH40.1 immunostaining while preincubation with the extract not containing the fusion protein had no effect. Thus, the reaction of AH40.1 with the p40-producing cells was apparently specific for p40. Only p40 was recognized by AH40.1 on Western blots and the binding was abolished by absorption with the fusion protein.

Normal cells within the tumor mass did not react with AH40.1 and an immunohistochemical screening of over 20 normal tissues also failed to detect any reactivity, with one exception; there is apparently a species of antibody in the antiserum that reacts with an 18 kd protein found in skeletal muscle. However, absorption with an acetone powder of skeletal muscle obliterated the reactivity on skeletal muscle tissue sections, but not on the testicular cancer specimens. Thus, when properly absorbed, AH40.1 appears quite specific for malignant cells.

EXAMPLE 1

In Vitro Translation

Because several features of the 5' L1Hs leader, including its length, potential secondary structure, and the presence of two short ORFs, might interfere with efficient translation, we initially tested the translatability of several L1Hs RNAs in vitro. Earlier reports (Skowronski, J. et al., (1985) Proc. Natl. Acad. Sci. USA 82, 6050–6054; and Skowronski, J. et al., (1988) Mol. Cell. Biol. 8, 1385–1397) described 10 cDNAs representing the polyadenylylated, cytoplasmic L1Hs RNAs in NTera2D1 cells; the complete sequence of cD11 and partial sequences for the others were reported. Although the cDNAs are approximately full length (6.5 kbp), none contains a complete 5' terminus. Comparison of the sequences of the 5' ends of several of the cDNA clones—cD11, cD12, cD14, and cD16—with that of the genomic consensus sequence indicates that they begin at residue 33 (Skowronski, J. et al., (1988) Mol. Cell. Biol. 8, 1385–1397), 14, 29, and 12, respectively.

Figure 2:
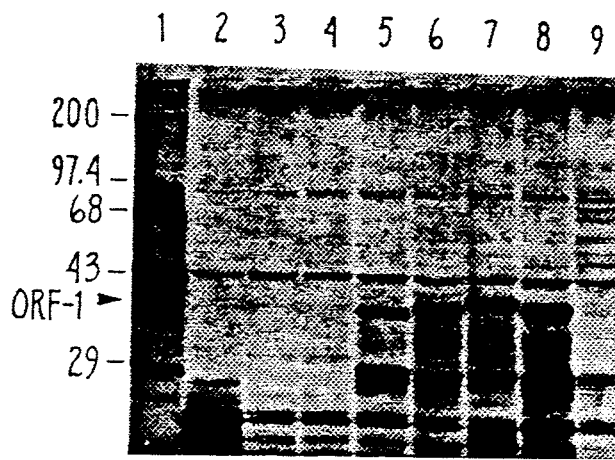
FIG. 2. In vitro translation of in vitro synthesized L1 RNAs. Approximately 50% of each reaction mixture was electrophoresed in a 10% Laemmli gel. The ≃44-kDa band seen in all experimental lanes is an artifact of the translation system. Lane 1, radiographic protein markers (Amersham) with sizes indicated in kilodaltons; lane 2, no-RNA control; lane 3, capped, sense RNA from p23A that was cleaved in the 5' untranslated region; lane 4, capped, antisense RNA from p23A; lane 5, full-length, capped, sense RNA from p16A; lane 6, full-length, capped, sense RNA from p23A; lane 7, full-length, capped, sense RNA from p11A; lane 8, full-length, capped, sense RNA from p>1; lane 9, full-length, capped sense RNA from pL1.1. The approximate size of the expected ORF1 translation product is indicated.

Capped, sense-strand RNA was synthesized from several of these cDNA sequences (contained in the Bluecript pKS(+) vector]and then tested for translatability in a rabbit reticulocyte lysate system. p11A, p16A, an p23A gave major polypeptide products of the approximate size predicted for ORF1 (FIG. 2, lanes 7, 5 and 6, respectively). Neither p12A nor p14A yielded a product corresponding to ORF1, suggesting the possibility of termination codons early in ORF1. The RNA synthesized from cD11, which was known from sequence analysis to have a completely open ORF1(12), yielded the largest polypeptide. The proteins derived from p16A and p23A were slightly smaller, consistent with premature, nonconsensus stop codons or small deletions within the ORF1s of these two cDNAs.

Deleted derivatives of p11A were employed to confirm that the major polypeptide was a product of ORF1 translation. RNA was prepared both from P11ASac, which lacks a small portion of the 3' end of ORF1 as well as all of ORF2 (FIG. 1c), and from p11AKpn, which lacks ORF1 (FIG. 1d). In both instances the major 40-kDa polypeptide disappeared; translation of p11ASac yielded an appropriately shorter ORF1 product, but no polypeptide corresponding to ORF1 was produced by translation of p11AKpn RNA. Thus, the ≈40-kDa polypeptide seen in FIG. 2 is the product of ORF1 translation and that the 5' leader does not block translation.

The coding potential of two genomic clones was also assessed. In vitro translation of the capped, sense RNA prepared using pλ1 resulted in the production of a putative ORF1 polypeptide of ≈39 kDa (FIG. 2, lane 8). The second genomic L1Hs, pL1.1, contains a base-pair deletion that causes a frame shift immediately after the first methionine residue of ORF1, which probably explains why the translation of the pL1.1 sense RNA yields no detectable ORF1 product (FIG. 2, lane 9).

In addition to the putative ORF1 products, several other polypeptides are produced during translation of RNA from the various cDNAs and genomic clones (FIG. 2). Whether these represent alternative initiation events, ORF2 polypeptides, or proteolytic degradation products is unclear.

EXAMPLE 2

Western Blot Analysis of Human Cell Extracts

Figure 3B:
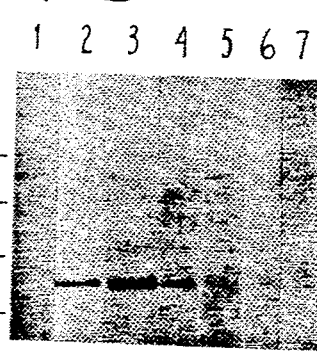

The preadsorbed antiserum was used to screen several human cell lines for the presence of the protein encoded by L1Hs ORF1. The preadsorbed antiserum recognized an ≈38-kDa polypeptide in extracts of NTera2D1 cells (FIG. 3B, lane 2) as well as in extracts of another human teratocarcinoma cell line, 2102Ep (lane 3), and of the choriocarcinoma cell line JEG-3 (lane 4). The polypeptide was most abundant in 2102Ep cells. Low amounts of a reactive 38-kDa polypeptide were just detectable in 293 cells (lane 5) and HeLa cells (lane 6). No reactive 38-kDA protein was visualized with a matched, preadsorbed, preimmune serum in NTera2D1 extracts (FIG. 3B, lane 1) or in any other cell extracts. These data suggest that several, but not all, human cell lines contain differing amounts of an ORF1 polypeptide.

Figure 4A:
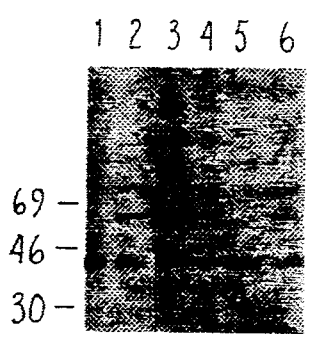
FIGS. 4A-4B. Western blot analysis of transfected NTera2D1 extracts. NTera2D1 cells were harvested 60 hr after transfection. Extraction was carried out as described in the text; supernatants (odd lanes) and pellets (even lanes) obtained form a 10,000 × g centrifugation of the suspension were examined. In each case, protein from ≃$10^5$ cells was subjected to electrophoresis under denaturing conditions in a 7% Laemmli gel. Blots were probed with preadsorbed HS1 antiserum (FIG. 4A) and with the corresponding preimmune serum (FIG. 4B). Sizes of protein markers are indicated. Transfections were carried out with unmodified pGEM-5Zf vector (FIG. 4A) lanes 1 and 2); p1LZ.
Figure 4B:

Additional evidence for the identification of the NTera2D1 38-kDa polypeptide with the ORF1 product was obtained in transient-transfection experiments using p1LZ and p3LZ (FIG. 1 i and j). Specific L1Hs RNAs are transcribed form these vectors in NTera2D1 cells. Both plasmids contain a full-length, ≈900-bp, L1Hs 5' leader region cloned into the Bluescript vector. In p1LZ, the E. coli 1 acZ gene is fused, in frame, to the first few ORF1 codons so that no ORF1 polypeptide can be made. p3LZ contains the entire open ORF1 polypeptide can be made. p3LZ contains the entire open ORF1 derived from cD11 and the lacZ gene is fused, in frame, following the first few ORF2 codons. The sequence of cD11 predicts an ORF1 polypeptide of 39.8 kDa. Using preadsorbed antiserum. Western blot analysis of extracts from NTera2D1 cells transfected with either unmodified pGEM-5Zf (FIG. 4A, lanes 1 and 2) or p1LZ (lanes 3 and 4) as controls demonstrated the presence of the ≈38-kDA endogenous polypeptide already described. The major portion of this L1Hs ORF1 protein was present in the 10,000 × g supernatant fraction of the extracts (FIG. 4A, compare lanes 1 and 2 or lanes 3 and 4). In extracts of cells transfected with p3LZ, this same polypeptide as well as one ≈2 kDa larger reacted with the antiserum (lanes 5 and 6) and was, again, most abundant in the 10,000 × g supernatant fraction. Neither of these proteins was recognized by the corresponding preimmune serum (FIG. 4B, lanes 1 and 2). In each case, the Western blots showed three NTera2D1 proteins ranging from 60 to 90 kDa (FIG. 4A) that were also recognized by the preadsorbed preimmune serum (FIG. 4B, lanes 1 and 2).

Figure 5A:
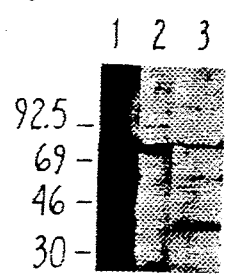
FIGS. 5A–5B. Competition study. Twenty micrograms of protein from *E. coli* transfected with p3HS1 (lanes 1) or p3HS3 (lanes 2) and 43 μg of protein from NTera2D1 cells transfected with p1LZ (lanes 3) were subjected to electrophoresis and blotting. Blots were probed with preadsorbed HS1 antiserum at a 1:1000 dilution (FIG. 5A) and with this same antiserum additionally preadsorbed with the fusion protein contained in 1 ml of culture of E. coli transfected with p3HS1 (FIG. 5B).
Figure 5B:
Figure 6A:
FIGS. 6A–6D. Immunostaining of human testicular germ cell tumors with the AH40.1 antibody.
Figure 6B:
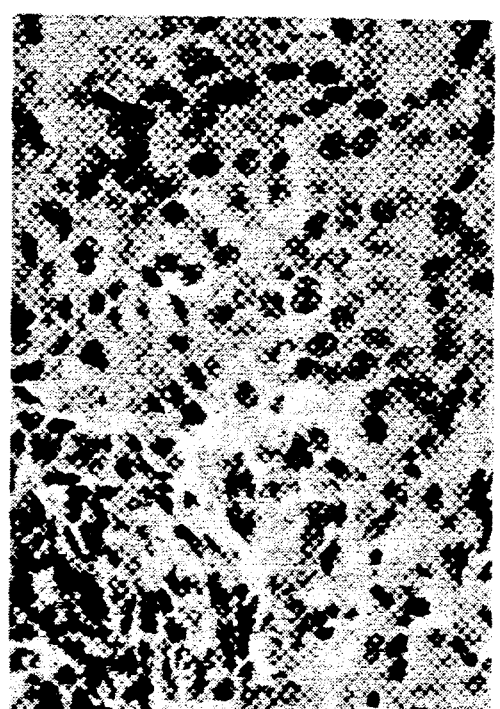
Figure 6C:
Figure 6D:
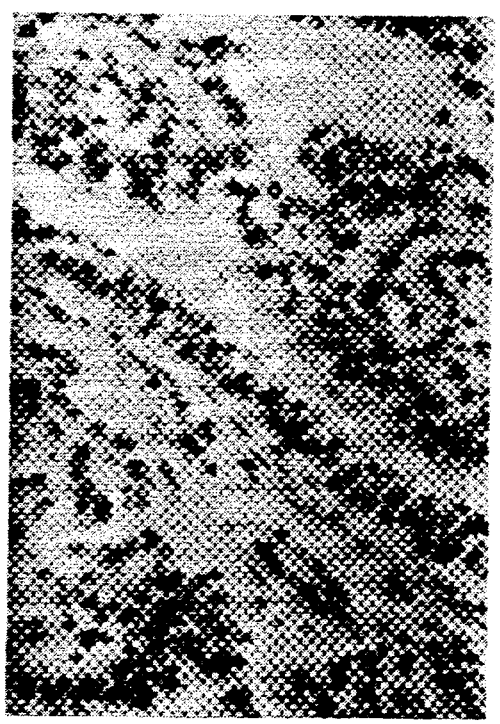

To confirm the identity of 38-kDa protein visualized by Western blot analysis, competition studies were carried out using the trpE-L1HsORF1 fusion protein. The fusion protein competed with the 38-kDa endogenous protein for antibody binding, as expected if the 38-kDa protein is indeed the L1Hs ORF1-encoded protein (FIG. 5). In addition, extracts of untransfected NTera2D1 cells competed with both the 38-kDa and the 40-kDa proteins in extracts from p3LZ-transfected NTera2D1 cells for recognition by the antiserum, as demonstrated by Western blot analysis. These results are expected if both the 38- and 40-kDa polypeptides are encoded by L1Hs ORF1.

These experiments suggest that several human cell lines contain an ORF1 polypeptide. The electrophoretic mobility of the endogenous L1Hs ORF1 product is similar in all cell lines tested, and slightly greater than that of the cD11 ORF1 product.

EXAMPLE 3

Analyses with AH40.1

A polyclonal antibody, AH40.1, developed against p40 was used to immunohistochemically examine 59 human testicular germ cell tumors, most of which contained two or more histologic subtypes (e.g., embryonal carcinoma, yolk sac tumor, teratoma). Six of the 59 samples were immunoreactive and preimmune serum from the AH40.1-producing rabbit was non-reactive when substituted for the primary antiserum. In five of the six positive specimens the cells expressing p40 were very similar: they were epithelial and appeared undifferentiated with the very large, irregular nuclei, prominent nucleoli and indistinct cell membranes characteristic of embryonal carcinoma or yolk sac tumor cells (FIG. 1A, 1B).

One case did not fit the general description. This was a tumor containing two types of L1Hs-expressing cells, one of which appeared like those described above: undifferentiated with very large, irregular nuclei and indistinct cell membranes. The other cell type appeared more elongated and had formed epithelial structures resembling glands (FIG. 1C, 1D).

One of the positive cases presented with metastases to the lung and lymph nodes. Examination of these tissues with AH40.1 demonstrated that they, too, were positive for p40. As with the primary tumor, the L1Hs-positive cells had the very undifferentiated appearance of yolk sac tumor cells and the degree of immunostaining was similar to that seen in the primary tumor.

2102Ep teratocarcinoma cell extracts are p40-positive by Western blotting. p40-containing, nonformalin-fixed 2102Ep cells reacted with AH40.1, but the staining was greatly reduced if the cells were first fixed with formalin. It appeared that the degree of staining was reduced by a factor of 4-6-fold by formalin fixation. This result implies that while we have identified only 6 positive cases among the 59 examined, there may in fact be many more tumors actively expressing L1Hs, but at levels below our detection threshold.

All publications mentioned hereinabove are hereby incorporated in their entirety by reference. In particular, Leibold, D. M. et al. (Sep. 1990) Proc. Natl. Acad. Sci. USA 87:6990–6994 is hereby incorporated in its entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An antibody having binding affinity to the p40, protein produced by the line-1 ORF1 gene, wherein said antibody specifically binds p40 protein produced by testicular cancer cells in the presence of normal cells.

2. The antibody according to claim 1, wherein said antibody is a polyclonal antibody.

3. The antibody according to claim 1, wherein said antibody is a monoclonal antibody.

4. A hybridoma which produces the monoclonal antibody according to claim 4.

5. The hybridoma according to claim 5, wherein said hybridoma results from the fusion of a myeloma cell and a spleen cell.

6. The hybridoma according to claim 6, wherein said myeloma cell is derived from a mouse.

7. A diagnostic kit comprising:
   i) at least one antibody according to claim 1, and
   ii) a conjugate comprising a binding partner of said antibody and a label.

8. The kit of claim 7 wherein said antibody is polyclonal.

9. The kit of claim 7 wherein said antibody is monoclonal.

* * * * *

UNITED STATES PATENT AND TRADEMARK OFFICE
CERTIFICATE OF CORRECTION

PATENT NO. : 5,280,108
DATED : January 18, 1994
INVENTOR(S) : Thomas G. Fanning

It is certified that error appears in the above-indentified patent and that said Letters Patent is hereby corrected as shown below:

Column 10, lines 48-58, claims 4-7, should read as follow:

4. A hybridoma which produces the monoclonal antibody according to Claim 3.

5. The hybridoma according to Claim 4, wherein said hybridoma results from the fusion of a myeloma cell and a spleen cell.

6. The hybridoma according to claim 5, wherein said myeloma cell is derived from a mouse.

7. A diagnostic kit comprising: an antibody against the p40 protein produced by the Line-1 ORF1 gene according to Claim 1, wherein said antibody specifically binds p40 protein produced by testicular cancer cells in the presence of normal cells and a label.

Signed and Sealed this

Thirtieth Day of August, 1994

Attest:

BRUCE LEHMAN

Attesting Officer     Commissioner of Patents and Trademarks